US011311750B2

(12) United States Patent
Zannoni et al.

(10) Patent No.: US 11,311,750 B2
(45) Date of Patent: Apr. 26, 2022

(54) LUBRICATING MEMBER FOR RAZOR CARTRIDGES COMPRISING METATHESIZED UNSATURATED POLYOLS

(71) Applicant: The Gillette Company LLC, Boston, MA (US)

(72) Inventors: Luke Andrew Zannoni, West Chester, OH (US); Beth Ann Schubert, Mainville, OH (US); Rajan Keshav Panandiker, West Chester, OH (US); Joseph Jay Kemper, Cincinnati, OH (US); Robert John Strife, West Chester, OH (US); Safa Motlagh, Dayton, OH (US); Jeffrey John Scheibel, Glendale, OH (US); Alison Fiona Stephens, Maidenhead (GB); Philip Andrew Sawin, Cincinnati, OH (US)

(73) Assignee: The Gillette Company LLC, Boston, MA (US)

( * ) Notice: Subject to any disclaimer, the term of this patent is extended or adjusted under 35 U.S.C. 154(b) by 180 days.

(21) Appl. No.: 15/632,662

(22) Filed: Jun. 26, 2017

(65) Prior Publication Data
US 2018/0008843 A1 Jan. 11, 2018

Related U.S. Application Data

(60) Provisional application No. 62/359,793, filed on Jul. 8, 2016.

(51) Int. Cl.
| | | |
|---|---|---|
| *C10M 107/24* | (2006.01) | |
| *A61Q 19/00* | (2006.01) | |
| *A61Q 9/02* | (2006.01) | |
| *C10M 109/02* | (2006.01) | |
| *A61K 8/86* | (2006.01) | |
| *A61K 8/60* | (2006.01) | |
| *C08L 23/02* | (2006.01) | |
| *C10M 105/42* | (2006.01) | |
| *C11D 3/20* | (2006.01) | |
| *C10N 20/04* | (2006.01) | |
| *C10N 20/00* | (2006.01) | |
| *C10N 30/06* | (2006.01) | |

(52) U.S. Cl.
CPC ............ *A61Q 19/002* (2013.01); *A61K 8/602* (2013.01); *A61K 8/86* (2013.01); *A61Q 9/02* (2013.01); *A61Q 19/005* (2013.01); *C08L 23/02* (2013.01); *C10M 105/42* (2013.01); *C10M 107/24* (2013.01); *C10M 109/02* (2013.01); *C08L 2205/025* (2013.01); *C10M 2209/0606* (2013.01); *C10N 2020/013* (2020.05); *C10N 2020/04* (2013.01); *C10N 2030/06* (2013.01); *C11D 3/2093* (2013.01)

(58) Field of Classification Search
None
See application file for complete search history.

(56) References Cited

U.S. PATENT DOCUMENTS

| | | |
|---|---|---|
| 6,442,839 B1 | 9/2002 | Tseng et al. |
| 2007/0110703 A1 | 5/2007 | Ogrady et al. |
| 2008/0060201 A1 | 3/2008 | Kwiecien |
| 2009/0223057 A1 | 9/2009 | Coope-Epstein et al. |
| 2011/0197447 A1 | 8/2011 | Stephens et al. |
| 2011/0197448 A1 | 8/2011 | Stephens et al. |
| 2011/0197449 A1 | 8/2011 | Stephens et al. |
| 2013/0118014 A1 | 5/2013 | Stephens et al. |
| 2013/0280174 A1 | 10/2013 | Lipic et al. |
| 2013/0281551 A1 | 10/2013 | Stella et al. |
| 2014/0357714 A1* | 12/2014 | Braksmayer ......... A23D 7/0053 514/547 |
| 2014/0366381 A1 | 12/2014 | Phipps et al. |
| 2015/0105566 A1 | 4/2015 | Cohen et al. |
| 2016/0177217 A1* | 6/2016 | Moloney .............. C10M 107/30 508/107 |
| 2016/0177218 A1 | 6/2016 | Moloney et al. |
| 2017/0009402 A1 | 1/2017 | Mohammadi et al. |

OTHER PUBLICATIONS

PCT International Search Report with Written Opinion in corresponding international application PCT/US2017/041019 dated Sep. 18, 2017.

* cited by examiner

*Primary Examiner* — Brian Gulledge
(74) *Attorney, Agent, or Firm* — Kevin C. Johnson

(57) ABSTRACT

The invention relates to a lubricating member for a razor cartridge comprising a metathesized unsaturated polyol ester for improved lubrication.

16 Claims, No Drawings

LUBRICATING MEMBER FOR RAZOR CARTRIDGES COMPRISING METATHESIZED UNSATURATED POLYOLS

FIELD OF THE INVENTION

The invention relates to a lubricating member for razor cartridges comprising a metathesized unsaturated polyol ester exhibiting improved lubricating properties.

BACKGROUND OF THE INVENTION

The use of shaving aids in combination with razor blades to provide lubrication benefits during the shave is known, see for example U.S. Pat. Nos. 7,121,754; 6,298,558; 5,711,076; 5,134,775; 6,301,785; U.S. 2009/0223057; U.S. 2006/0225285; WO2007/031793; U.S. 2104/0323374 and GB1299089. Such shaving aids typically comprise a water-insoluble matrix material to provide structural integrity and a water-soluble polymer, such as polyethylene oxide (polyox), in order to provide lubrication during the shave once the water-soluble polymer forms a solution with the water present during shaving. Since the introduction of polyox as a shaving lubricant, little development has been made in the field, even though polyethylene oxide polymers are not without limitations. For example, utilizing polyethylene oxide polymers having low molecular weights or high molecular weights may improve and provide a means to improve lubrication, but may also result in trade off with regards to residue and/or stringiness or other aspects of the aqueous solution typically formed in-use. The resultant viscosity in aqueous solution may also increase, leading to negatively perceived attributes, for example concerning the feeling of the shave for the user, particularly in respect of the lubricant. The prior art also describes the use of combinations of high and low molecular weight polyethylene oxide polymers in order to balance these performance attributes. Nevertheless, such combinations are also limited in their ability to improve performance and/or suffer from other negative performance attributes. The art further describes the incorporation of additional materials to further improve the lubrication performance. For example, U.S. Pat. No. 6,442,839; U.S. 2007/0110703 and U.S. 2009/0223057 describe the use of low levels of mineral and essential oils, butters, waxes and silicones. The use of mineral oil to enhance the glide performance is described in U.S. 2008/0060201. However, the art also discloses a reduction of the swelling and solubility of the water soluble shaving aid contained in the water insoluble polymer matrix. The ability of the shaving aid to swell in contact with water is however believed to be the key mechanism by which the lubrication benefit is delivered to the skin. Hence this is not desirable, as it will negatively impact the overall performance.

Consequently, there is still a need to provide a lubricating member for razor cartridges comprising a water soluble polymer exhibiting improved lubricating properties which can be readily manufactured without impacting performance.

Metathesized unsaturated polyol esters have been described in the literature to improve the performance of foaming composition as described for example in U.S. 2013/0280174. It is now found that these materials have utility in lubricating members. It is recognized that the problems with commercially available metathesized unsaturated polyol esters lay in the rheology of such materials as such rheology resulted in a range of spreading that was insufficient with a first class of materials and excessive spreading with a second class of materials. Thus, both classes of commercially available materials exhibited insufficient spreading leading to poor lubrication and feel during the shaving process. Versions of metathesized unsaturated polyol esters are disclosed that have the correct rheology. Such species of metathesized unsaturated polyol esters provide unexpectedly improved skin conditioning benefits after the shave and lubrication during the shave. Additionally, these materials are tolerant to the wide range of conditions experienced during the shave such as the high pH from shaving gels and foams and provide synergistic benefits in the presence of cationic polymeric materials.

SUMMARY OF THE INVENTION

One aspect of the invention relates to a lubricating member for use on a hair removal device, said lubricating member comprising a lubricating material comprising from 1 to 99% by weight of a metathesized unsaturated polyol esters.

DETAILED DESCRIPTION OF THE INVENTION

Definitions

The terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

The term "natural oil derivatives" refers to derivatives thereof derived from natural oil. The methods used to form these natural oil derivatives may include one or more of addition, neutralization, overbasing, saponification, transesterification, esterification, amidification, hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification or a combination of two or more thereof. Examples of natural derivatives thereof may include carboxylic acids, gums, phospholipids, soapstock, acidulated soapstock, distillate or distillate sludge, fatty acids, fatty acid esters, as well as hydroxy substituted variations thereof, including unsaturated polyol esters. In some embodiments, the natural oil derivative may comprise an unsaturated carboxylic acid having from about 5 to about 30 carbon atoms, having one or more carbon-carbon double bonds in the hydrocarbon (alkene) chain. The natural oil derivative may also comprise an unsaturated fatty acid alkyl (e.g., methyl) ester derived from a glyceride of natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil).

The term "free hydrocarbon" refers to any one or combination of unsaturated or saturated straight, branched, or cyclic hydrocarbons in the $C_2$ to $C_{22}$ range.

The term "metathesis monomer" refers to a single entity that is the product of a metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis).

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds. In some embodiments, the term "metathesis oligomer" may include metathesis reactions wherein greater than ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing greater than ten bonded groups derived from the reactant compounds.

As used herein, the terms "metathesize" and "metathesizing" may refer to the reacting of a unsaturated polyol ester feedstock in the presence of a metathesis catalyst to form a metathesized unsaturated polyol ester product comprising a new olefinic compound and/or esters. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming an oligomer having a new mixture of olefins and esters that may comprise one or more of: metathesis monomers, metathesis dimers, metathesis trimers, metathesis tetramers, metathesis pentamers, and higher order metathesis oligomers (e.g., metathesis hexamers, metathesis, metathesis heptamers, metathesis octamers, metathesis nonamers, metathesis decamers, and higher than metathesis decamers and above).

As used herein, the term "polyol" means an organic material comprising at least two hydroxy moieties.

As used herein, the articles including "a" and "an" when used in a claim, are understood to mean one or more of what is claimed or described.

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Compositions, Articles, Methods of Use and Treated Articles

TABLE 1

Compositions

| Comp. No. | Composition |
|---|---|
| 1 | A composition comprising, <br> a) a metathesized unsaturated polyol ester, said metathesized unsaturated polyol ester having one or more of the following properties: <br> (i) a weight average molecular weight of from about 5,000 Daltons to about 50,000 Daltons, from about 5,500 Daltons to about 50,000 Daltons, from about 5,500 Daltons to about 40,000 Daltons, or from about 6,000 Daltons to about 30,000 Daltons; <br> (ii) an oligomer index from greater than 0 to 1, from 0.001 to 1, 0.01 to 1, or from 0.05 to 1; <br> (iii) an iodine value of from about 30 to about 200, from about 30 to about 150, from about 30 to about 120, or from about 50 to about 110. |
| 2 | In one aspect of said composition 1 of Table 1, said metathesized unsaturated polyol ester has the weight average molecular weight property from a)(i) above. |
| 3 | In one aspect of said composition 1 of Table 1, said metathesized unsaturated polyol ester has the oligomer index property from a)(ii) above. |
| 4 | In one aspect of said composition 1 of Table 1, said metathesized unsaturated polyol ester has the iodine value property from a)(iii) above. |
| 5 | In one aspect of said composition 1 of Table 1, said metathesized unsaturated polyol ester has the property from a)(i) and from a)(ii) above. |
| 6 | In one aspect of said composition 1 of Table 1, said metathesized unsaturated polyol ester has the properties from a)(i) and from a)(iii) above. |
| 7 | In one aspect of said composition 1 of Table 1, said metathesized unsaturated polyol ester has the properties from a)(ii) and from a)(iii) above. |
| 8 | In one aspect of said composition 1 of Table 1, said metathesized unsaturated polyol ester has the properties from a)(i), a)(ii) and from a)(iii) above. |

TABLE 1-continued

Compositions

| Comp. No. | Composition |
|---|---|
| 9 | In one aspect, of compositions 1, 2, 3, 4, 5, 6, 7, and 8 of Table 1, said metathesized unsaturated polyol ester has a free hydrocarbon content, based on total weight of metathesized unsaturated polyol ester, of from about 0% to about 5%, from about 0.1% to about 5%, from about 0.1% to about 4%, or from about 0.1 to about 3%. |
| 10 | In one aspect of Table 1 Compositions 1, 2, 3, 4, 5, 6, 7, 8, and 9 the metathesized unsaturated polyol ester is metathesized at least once. |
| 11 | In one aspect, of compositions 1, 2, 3, 4, 5, 6, 7, 8, 9 and 10 of Table 1, said composition comprises, based on total composition weight, from about 0.1% to about 50%, from about 0.5% to about 30%, or from about 1% to about 20% of said metathesized unsaturated polyol ester. |

TABLE 2

Compositions

| Comp. No. | Composition |
|---|---|
| 1 | A composition comprising: <br> a) a metathesized unsaturated polyol ester, said metathesized unsaturated polyol ester having a weight average molecular weight of from about 2,000 Daltons to about 50,000 Daltons, from about 2,500 Daltons to about 50,000 Daltons, from about 3,000 Daltons to about 40,000 Daltons, from about 3,000 Daltons to about 30,000 Daltons; and one or more of the following properties: <br> (i) a free hydrocarbon content, based on total weight of metathesized unsaturated polyol ester, of from about 0% to about 5%, from about 0.1% to about 5%, from about 0.1% to about 4%, or from about 0.1 to about 3%; <br> (ii) an oligomer index from greater than 0 to 1, from 0.001 to 1, 0.01 to 1, or from 0.05 to 1; <br> (iii) an iodine value of from about 8 to about 200, from about 10 to about 200, from about 20 to about 150, from about 30 to about 120. |
| 2 | In one aspect of said composition 1 of Table 2, said metathesized unsaturated polyol ester has the free hydrocarbon content property from a)(i) above. |
| 3 | In one aspect of said composition 1 of Table 2, said metathesized unsaturated polyol ester has the oligomer index property from a)(ii) above. |
| 4 | In one aspect of said composition 1 of Table 2, said metathesized unsaturated polyol ester has the iodine value property from a)(iii) above. |
| 5 | In one aspect of said composition 1 of Table 2, said metathesized unsaturated polyol ester has the property from a)(i) and from a)(ii) above. |
| 6 | In one aspect of said composition 1 of Table 2, said metathesized unsaturated polyol ester has the properties from a)(i) and from a)(iii) above. |
| 7 | In one aspect of said composition 1 of Table 2, said metathesized unsaturated polyol ester has the properties from a)(ii) and from a)(iii) above. |
| 8 | In one aspect of said composition 1 of Table 2, said metathesized unsaturated polyol ester has the properties from a)(i), a)(ii) and from a)(iii) above. |
| 9 | In one aspect of Table 2 Compositions 1, 2, 3, 4, 5, 6, 7, and 8 the metathesized unsaturated polyol ester is metathesized at least once. |
| 10 | In one aspect, of compositions 1, 2, 3, 4, 5, 6, 7, and 9 of Table 2, said composition comprises, based on total composition weight, from about 0.1% to about 50%, from about 0.5% to about 30% or from about 1% to about 20% of said metathesized unsaturated polyol ester. |

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is derived from a natural polyol ester and/or a synthetic polyol ester, in one aspect, said natural polyol ester is selected from the group consisting of a vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is selected from the group consisting of metathesized Abyssinian oil, metathesized Almond Oil, metathesized Apricot Oil, metathesized Apricot Kernel oil, metathesized Argan oil, metathesized Avocado Oil, metathesized Babassu Oil, metathesized Baobab Oil, metathesized Black Cumin Oil, metathesized Black Currant Oil, metathesized Borage Oil, metathesized Camelina oil, metathesized Carinata oil, metathesized Canola oil, metathesized Castor oil, metathesized Cherry Kernel Oil, metathesized Coconut oil, metathesized Corn oil, metathesized Cottonseed oil, metathesized Echium Oil, metathesized Evening Primrose Oil, metathesized Flax Seed Oil, metathesized Grape Seed Oil, metathesized Grapefruit Seed Oil, metathesized Hazelnut Oil, metathesized Hemp Seed Oil, metathesized Jatropha oil, metathesized Jojoba Oil, metathesized Kukui Nut Oil, metathesized Linseed Oil, metathesized Macadamia Nut Oil, metathesized Meadowfoam Seed Oil, metathesized Moringa Oil, metathesized Neem Oil, metathesized Olive Oil, metathesized Palm Oil, metathesized Palm Kernel Oil, metathesized Peach Kernel Oil, metathesized Peanut Oil, metathesized Pecan Oil, metathesized Pennycress oil, metathesized Perilla Seed Oil, metathesized Pistachio Oil, metathesized Pomegranate Seed Oil, metathesized Pongamia oil, metathesized Pumpkin Seed Oil, metathesized Raspberry Oil, metathesized Red Palm Olein, metathesized Rice Bran Oil, metathesized Rosehip Oil, metathesized Safflower Oil, metathesized Seabuckthorn Fruit Oil, metathesized Sesame Seed Oil, metathesized Shea Olein, metathesized Sunflower Oil, metathesized Soybean Oil, metathesized Tonka Bean Oil, metathesized Tung Oil, metathesized Walnut Oil, metathesized Wheat Germ Oil, metathesized High Oleoyl Soybean Oil, metathesized High Oleoyl Sunflower Oil, metathesized High Oleoyl Safflower Oil, metathesized High Erucic Acid Rapeseed Oil, and mixtures thereof.

Methods of Making Compositions

The compositions of the present invention can be formulated into any suitable form and prepared by any process chosen by the formulator, non-limiting examples of which are described in U.S. Pat. No. 5,879,584 which is incorporated herein by reference. For example, the metathesized unsaturated polyol esters can be combined directly with the composition's other ingredients without pre-emulsification and/or pre-mixing to form the finished products. Alternatively, the metathesized unsaturated polyol esters can be combined with surfactants or emulsifiers, solvents, suitable adjuncts, and/or any other suitable ingredients to prepare emulsions prior to compounding the finished products.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (N.J., U.S.A.).

Metathesized Unsaturated Polyol Ester

Exemplary metathesized unsaturated polyol esters and their starting materials are set forth in U.S. Patent Applications U.S. 2009/0220443 A1, U.S. 2013/0344012 A1 and US 2014/0357714 A1, which are incorporated herein by reference. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation I.

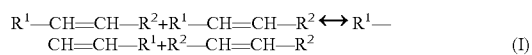
(I)

where $R^1$ and $R^2$ are organic groups.

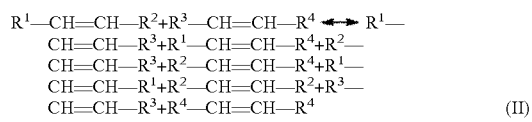
(II)

Cross-metathesis may be represented schematically as shown in Equation II.

where $R^1$, $R^2$, $R^3$, and $R^4$ are organic groups.

When a polyol ester comprises molecules having more than one carbon-carbon double bond, self-metathesis may result in oligomerization or polymerization of the unsaturates in the starting material. For example, Equation C depicts metathesis oligomerization of a representative species (e.g., a polyol ester) having more than one carbon-carbon double bond. In Equation C, the self-metathesis reaction results in the formation of metathesis dimers, metathesis trimers, and metathesis tetramers. Although not shown, higher order oligomers such as metathesis pentamers, hexamers, heptamers, octamers, nonamers, decamers, and higher than decamers, and mixtures of two or more thereof, may also be formed. The number of metathesis repeating units or groups in the metathesized natural oil may range from 1 to about 100, or from 2 to about 50, or from 2 to about 30, or from 2 to about 10, or from 2 to about 4. The molecular weight of the metathesis dimer may be greater than the molecular weight of the unsaturated polyol ester from which the dimer is formed. Each of the bonded polyol ester molecules may be referred to as a "repeating unit or group." Typically, a metathesis trimer may be formed by the cross-metathesis of a metathesis dimer with an unsaturated polyol ester. Typically, a metathesis tetramer may be formed by the cross-metathesis of a metathesis trimer with an unsaturated polyol ester or formed by the cross-metathesis of two metathesis dimers.

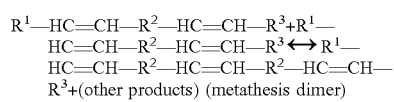

R¹—R²—HC=CH—R²—HC=CH—R³+R¹—
HC=CH—R²—HC=CH—R³ ↔ R¹—
HC=CH—R²—HC=CH—R²—HC=CH—
R²—HC=CH—R³+(other products) (metathesis trimer)

R¹—HC=CH—R²—HC=CH—R²—HC=CH—
R²—HC=CH—R³+R¹—HC=CH—
R²HC=CH—R³ ↔ R¹—HC=CH—R²—
HC=CH—R²—HC=CH—R²—HC=CH—
R²—HC=CH—R³+(other products) (metathsis tetramer)   Equation C where $R^1$, $R^2$, and $R^3$ are organic groups.

As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure (I):

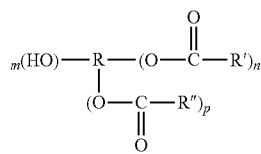

(I)

where n≥1;
m°0;
p≥0;
(n+m+p)≥2;
R is an organic group;
R' is an organic group having at least one carbon-carbon double bond; and
R" is a saturated organic group.

In many embodiments of the invention, the unsaturated polyol ester is an unsaturated polyol ester of glycerol. Unsaturated polyol esters of glycerol have the general structure (II):

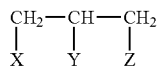

(II)

where —X, —Y, and —Z are independently selected from the group consisting of:

—OH; —(O—C(=O)—R'); and —(O—C(=O)—R");

where —R' is an organic group having at least one carbon-carbon double bond and —R" is a saturated organic group.

In structure (II), at least one of —X, —Y, and —Z is —(O—C(=O)—R').

In some embodiments, R' is a straight or branched chain hydrocarbon having about 50 or less carbon atoms (e.g., about 36 or less carbon atoms or about 26 or less carbon atoms) and at least one carbon-carbon double bond in its chain. In some embodiments, R' is a straight or branched chain hydrocarbon having about 6 carbon atoms or greater (e.g., about 10 carbon atoms or greater or about 12 carbon atoms or greater) and at least one carbon-carbon double bond in its chain. In some embodiments, R' may have two or more carbon-carbon double bonds in its chain. In other embodiments, R' may have three or more double bonds in its chain. In exemplary embodiments, R' has 17 carbon atoms and 1 to 3 carbon-carbon double bonds in its chain. Representative examples of R' include:

—(CH₂)₇CH=CH—(CH₂)₇—CH₃;

—(CH₂)₇CH=CH—CH₂—CH=CH—(CH₂)₄—CH₃; and

—(CH₂)₇CH=CH—CH₂—CH=CH₂—
CH=CH—CH—CH₂CH₃.

In some embodiments, R" is a saturated straight or branched chain hydrocarbon having about 50 or less carbon atoms (e.g., about 36 or less carbon atoms or about 26 or less carbon atoms). In some embodiments, R" is a saturated straight or branched chain hydrocarbon having about 6 carbon atoms or greater (e.g., about 10 carbon atoms or greater or about 12 carbon atoms or greater. In exemplary embodiments, R" has 15 carbon atoms or 17 carbon atoms.

Sources of unsaturated polyol esters of glycerol include synthesized oils, natural oils (e.g., vegetable oils, algae oils, bacterial derived oils, and animal fats), combinations of these, and the like. Recycled used vegetable oils may also be used. Representative non-limiting examples of vegetable oils include Abyssinian oil, Almond Oil, Apricot Oil, Apricot Kernel oil, Argan oil, Avocado Oil, Babassu Oil, Baobab Oil, Black Cumin Oil, Black Currant Oil, Borage Oil, Camelina oil, Carinata oil, Canola oil, Castor oil, Cherry Kernel Oil, Coconut oil, Corn oil, Cottonseed oil, Echium Oil, Evening Primrose Oil, Flax Seed Oil, Grape Seed Oil, Grapefruit Seed Oil, Hazelnut Oil, Hemp Seed Oil, Jatropha oil, Jojoba Oil, Kukui Nut Oil, Linseed Oil, Macadamia Nut Oil, Meadowfoam Seed Oil, Moringa Oil, Neem Oil, Olive Oil, Palm Oil, Palm Kernel Oil, Peach Kernel Oil, Peanut Oil, Pecan Oil, Pennycress oil, Perilla Seed Oil, Pistachio Oil, Pomegranate Seed Oil, Pongamia oil, Pumpkin Seed Oil, Raspberry Oil, Red Palm Olein, Rice Bran Oil, Rosehip Oil, Safflower Oil, Seabuckthorn Fruit Oil, Sesame Seed Oil, Shea Olein, Sunflower Oil, Soybean Oil, Tonka Bean Oil, Tung Oil, Walnut Oil, Wheat Germ Oil, High Oleoyl Soybean Oil, High Oleoyl Sunflower Oil, High Oleoyl Safflower Oil, High Erucic Acid Rapeseed Oil, combinations of these, and the like. Representative non-limiting examples of animal fats include lard, tallow, chicken fat, yellow grease, fish oil, emu oil, combinations of these, and the like. A representative non-limiting example of a synthesized oil includes tall oil, which is a byproduct of wood pulp manufacture. In some embodiments, the natural oil is refined, bleached, and/or deodorized.

Other examples of unsaturated polyol esters include esters such as those derived from ethylene glycol or propylene glycol, polyethylene glycol, polypropylene glycol, or poly (tetramethylene ether) glycol, esters such as those derived from pentaerythritol, dipentaerythritol, tripentaerythritol, trimethylolpropane, or neopentyl glycol, or sugar esters such as SEFOSE®. Sugar esters such as SEFOSE® include one or more types of sucrose polyesters, with up to eight ester groups that could undergo a metathesis exchange reaction. Sucrose polyesters are derived from a natural resource and therefore, the use of sucrose polyesters can result in a positive environmental impact. Sucrose polyesters are polyester materials, having multiple substitution positions around the sucrose backbone coupled with the chain length, saturation, and derivation variables of the fatty chains. Such sucrose polyesters can have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As sucrose polyesters are derived from a natural resource, a distribution in the IBAR and chain length may exist. For example, a sucrose polyester having an IBAR of 6, may contain a mixture of mostly IBAR of about 6, with some IBAR of about 5 and some IBAR of about 7. Additionally, such sucrose polyesters may have a saturation or iodine value ("IV") of about 3 to about 140. In another embodiment the sucrose polyester may have an IV of about 10 to about 120. In yet another embodiment the sucrose polyester may have an IV of about 20 to 100. Further, such sucrose polyesters have a chain length of about $C_{12}$ to $C_{20}$ but are not limited to these chain lengths.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter & Gamble Company of Cincinnati, Ohio.

Other examples of suitable polyol esters may include but not be limited to sorbitol esters, maltitol esters, sorbitan esters, maltodextrin derived esters, xylitol esters, polyglycerol esters, and other sugar derived esters.

Natural oils of the type described herein typically are composed of triglycerides of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a $C_{16}$ acid), and oleic acid (a $C_{18}$ acid); polyunsaturated acids include such fatty acids as linoleic acid (a di-unsaturated $C_{18}$ acid), linolenic acid (a tri-unsaturated $C_{18}$ acid), and arachidonic acid (a tetra-unsubstituted $C_{20}$ acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example, soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of oil. Therefore, for soybean oil, the average iodine value range is from 120-140. Soybean oil may comprise about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12octadecadienoic acid), and linolenic acid (9,12,15-octadecatrienoic acid).

In an exemplary embodiment, the vegetable oil is canola oil, for example, refined, bleached, and deodorized canola oil (i.e., RBD canola oil). Canola oil is an unsaturated polyol ester of glycerol that typically comprises about 95% weight or greater (e.g., 99% weight or greater) triglycerides of fatty acids. Major fatty acids in the polyol esters of canola oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Canola oil is a highly unsaturated vegetable oil with many of the triglyceride molecules having at least two unsaturated fatty acids (i.e., a polyunsaturated triglyceride).

In exemplary embodiments, an unsaturated polyol ester is self-metathesized in the presence of a metathesis catalyst to form a metathesized composition. Typically, after metathesis has occurred, the metathesis catalyst is removed from the resulting product. One method of removing the catalyst is treatment of the metathesized product with clay. In many embodiments, the metathesized composition comprises one or more of: metathesis monomers, metathesis dimers, metathesis trimers, metathesis tetramers, metathesis pentamers, and higher order metathesis oligomers (e.g., metathesis hexamers). A metathesis dimer refers to a compound formed when two unsaturated polyol ester molecules are covalently bonded to one another by a self-metathesis reaction. In many embodiments, the molecular weight of the metathesis dimer is greater than the molecular weight of the individual unsaturated polyol ester molecules from which the dimer is formed. A metathesis trimer refers to a compound formed when three unsaturated polyol ester molecules are covalently bonded together by metathesis reactions. In many embodiments, a metathesis trimer is formed by the cross-metathesis of a metathesis dimer with an unsaturated polyol ester. A metathesis tetramer refers to a compound formed when four unsaturated polyol ester molecules are covalently bonded together by metathesis reactions. In many embodiments, a metathesis tetramer is formed by the cross-metathesis of a metathesis trimer with an unsaturated polyol ester. Metathesis tetramers may also be formed, for example, by the cross-metathesis of two metathesis dimers. Higher order metathesis products may also be formed. For example, metathesis pentamers and metathesis hexamers may also be formed. The self-metathesis reaction also results in the formation of internal olefin compounds that may be linear or cyclic. If the metathesized polyol ester is fully or partially hydrogenated, the linear and cyclic olefins would typically be fully or partially converted to the corresponding saturated linear and cyclic hydrocarbons. The linear/cyclic olefins and saturated linear/cyclic hydrocarbons may remain in the metathesized polyol ester or they may be removed or partially removed from the metathesized polyol ester using one or more known stripping techniques, including but not limited to wipe film evaporation, falling film evaporation, rotary evaporation, steam stripping, vacuum distillation, etc.

In some embodiments, the unsaturated polyol ester is partially hydrogenated before being metathesized. For example, in some embodiments, the unsaturated polyol ester is partially hydrogenated to achieve an iodine value (IV) of about 120 or less before subjecting the partially hydrogenated polyol ester to metathesis.

In some embodiments, the unsaturated polyol ester may be hydrogenated (e.g., fully or partially hydrogenated) in order to improve the stability of the oil or to modify its viscosity or other properties. Representative techniques for hydrogenating unsaturated polyol esters are known in the art and are discussed herein.

In some embodiments, the natural oil is winterized. Winterization refers to the process of: (1) removing waxes and other non-triglyceride constituents, (2) removing naturally occurring high-melting triglycerides, and (3) removing high-melting triglycerides formed during partial hydrogenation. Winterization may be accomplished by known methods including, for example, cooling the oil at a controlled rate in order to cause crystallization of the higher melting components that are to be removed from the oil. The crystallized high melting components are then removed from the oil by filtration resulting in winterized oil. Winterized soybean oil is commercially available from Cargill, Incorporated (Minneapolis, Minn.).

In other embodiments, the metathesized unsaturated polyol esters can be used as a blend with one or more fabric care benefit agents and/or fabric softening actives.

Method of Making Metathesized Unsaturated Polyol Ester

The self-metathesis of unsaturated polyol esters is typically conducted in the presence of a catalytically effective amount of a metathesis catalyst. The term "metathesis catalyst" includes any catalyst or catalyst system that catalyzes a metathesis reaction. Any known or future-developed metathesis catalyst may be used, alone or in combination with one or more additional catalysts. Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru or W. These include first and second-generation Grubbs catalysts, Grubbs-Hoveyda catalysts, and the like. Suitable alkylidene catalysts have the general structure:

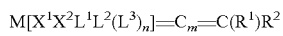

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

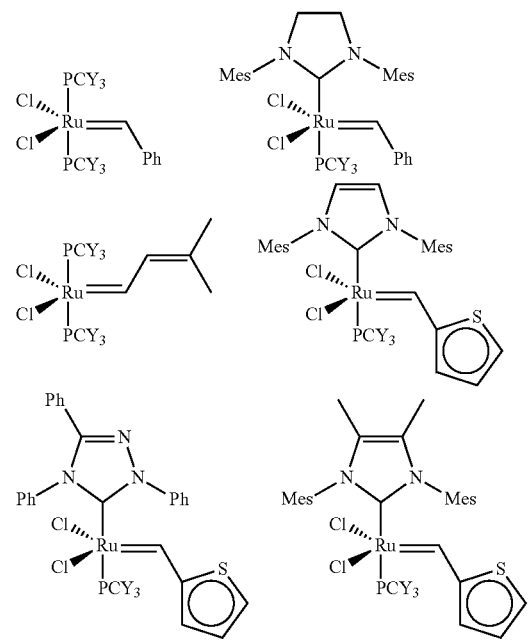

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

In certain embodiments, prior to the metathesis reaction, the unsaturated polyol ester feedstock may be treated to render the natural oil more suitable for the subsequent metathesis reaction. In one embodiment, the treatment of the unsaturated polyol ester involves the removal of catalyst poisons, such as peroxides, which may potentially diminish the activity of the metathesis catalyst. Non-limiting examples of unsaturated polyol ester feedstock treatment methods to diminish catalyst poisons include those described in PCT/US2008/09604; PCT/US2008/09635; and U.S. patent application Ser. Nos. 12/672,651 and 12/672,652, herein incorporated by reference in their entireties. In certain embodiments, the unsaturated polyol ester feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the unsaturated polyol ester feedstock with nitrogen, wherein the nitrogen gas is pumped into the feedstock treatment vessel at a pressure of approximately 10 atm (150 psig).

In certain embodiments, the unsaturated polyol ester feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, and combinations thereof.

In certain embodiments, the unsaturated polyol ester feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the unsaturated polyol ester feedstock's reactivity with the metathesis catalyst. Additional non-limiting examples of feedstock treatment are also described below when discussing the various metathesis catalysts.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 10 ppm, or about 2 ppm to about 5 ppm, of the metathesis catalyst per double bond of the starting composition (i.e., on a mole/mole basis) is used.

In some embodiments, the metathesis reaction is catalyzed by a system containing both a transition and a non-transition metal component. The most active and largest number of catalyst systems are derived from Group VI A transition metals, for example, tungsten and molybdenum.

Multiple, sequential metathesis reaction steps may be employed. For example, the metathesized unsaturated polyol ester product may be made by reacting an unsaturated polyol ester in the presence of a metathesis catalyst to form a first metathesized unsaturated polyol ester product. The first metathesized unsaturated polyol ester product may then be reacted in a self-metathesis reaction to form another metathesized unsaturated polyol ester product. Alternatively, the first metathesized unsaturated polyol ester product may be reacted in a cross-metathesis reaction with a unsaturated polyol ester to form another metathesized unsaturated polyol ester product. Also in the alternative, the transesterified products, the olefins and/or esters may be further metathesized in the presence of a metathesis catalyst. Such multiple and/or sequential metathesis reactions can be performed as many times as needed, and at least one or more times, depending on the processing/compositional requirements as understood by a person skilled in the art. As used herein, a "metathesized unsaturated polyol ester product" may include products that have been once metathesized and/or multiply metathesized. These procedures may be used to form metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers). These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups. In certain embodiments, it may be desirable to use the metathesized unsaturated polyol ester products produced by cross metathesis of an unsaturated polyol ester, or blend of unsaturated polyol esters, with a C2-C100 olefin, as the reactant in a self-metathesis reaction to produce another metathesized unsaturated polyol ester product. Alternatively, metathesized products produced by cross metathesis of an unsaturated polyol ester, or blend of unsaturated polyol esters, with a C2-C100 olefin can be combined with an unsaturated polyol ester, or blend of unsaturated polyol esters, and further metathesized to produce another metathesized unsaturated polyol ester product.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene. The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa). In certain embodiments, it may be desirable to run the metathesis reactions under an atmosphere of reduced pressure. Conditions of reduced pressure or vacuum may be used to remove olefins as they are generated in a metathesis reaction, thereby driving the metathesis equilibrium towards the formation of less volatile products. In the case of a self-metathesis of a natural oil, reduced pressure can be used to remove $C_{12}$ or lighter olefins including, but not limited to, hexene, nonene, and dodecene, as well as byproducts including, but not limited to cyclohexa-diene and benzene as the metathesis reaction proceeds. The removal of these species can be used as a means to drive the reaction towards the formation of diester groups and cross linked triglycerides.

Hydrogenation:

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a metathesized unsaturated polyol ester, and the metathesized unsaturated polyol ester is then hydrogenated (e.g., partially or fully hydrogenated) to form a hydrogenated metathesized unsaturated polyol ester.

Hydrogenation may be conducted according to any known method for hydrogenating double bond-containing compounds such as vegetable oils. In some embodiments, the unsaturated polyol ester or metathesized unsaturated polyol ester is hydrogenated in the presence of a nickel catalyst that has been chemically reduced with hydrogen to an active state. Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

In some embodiments, the hydrogenation catalyst comprising, for example, nickel, copper, palladium, platinum, molybdenum, iron, ruthenium, osmium, rhodium, or iridium. Combinations of metals may also be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt. % nickel.

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50 deg. C. to 350 deg. C., for example, about 100 deg. C. to 300 deg. C. or about 150 deg. C. to 250 deg. C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of H2 gas. Typically, the H2 gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120 deg. C. to 200 deg. C.) where it is maintained by cooling the reaction mass, for example, with cooling coils. When the desired degree of hydrogenation is reached, the reaction mass is cooled to the desired filtration temperature.

The amount of hydrogenation catalysts is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the H2 gas pressure. In some embodiments, the hydrogenation catalyst is used in an amount of about 10 wt. % or less, for example, about 5 wt. % or less or about 1 wt. % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter.

Representative examples of filtering aids include diatomaceous earth, silica, alumina, and carbon. Typically, the filtering aid is used in an amount of about 10 wt. % or less, for example, about 5 wt. % or less or about 1 wt. % or less. Other filtering techniques and filtering aids may also be employed to remove the used hydrogenation catalyst. In other embodiments the hydrogenation catalyst is removed using centrifugation followed by decantation of the product.

Lubricating Material: Water Soluble Polymer

According to the present invention, the lubricating member may comprise a lubricating material comprising from about 1% to about 99% by weight of water soluble polymer, preferably at least about 15%, more preferably at least about 20%, most preferably at least about 25%, and up to about 70%, preferably up to about 60% by weight of the lubricating member. The term water soluble polymer does not include the silicone polyether block copolymer as defined hereinafter.

Examples of suitable water soluble polymers include polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, copolymers of polyethylene oxide (PEO) and polypropylene oxide (PPO), guars, celluloses, modified celluloses and mixtures thereof. In some embodiments, said water soluble polymer is selected from high and or low molecular weight polyethylene oxides referred to in the industry as polyethylene oxide and polyethylene glycol respectively. Preferably the water soluble polymer is selected from the group consisting of polyethylene oxide, polyethylene glycol, copolymers of polyethylene oxide and polypropylene oxide and mixtures thereof.

The preferred water soluble polymers are the polyethylene oxides generally known as POLYOX (available from Union Carbide Corporation) or ALKOX (available from Meisei Chemical Works, Kyoto, Japan). The water soluble polymer, (especially these polyethylene oxides), may have average molecular weights of at least about 20,000, preferably at least about 50,000, more preferably at least about 100,000 or from about 100,000 to about 8 million, preferably about 300,000 to about 8 million, more preferably from about 1 million to about 5 million, even more preferably about 2 to 3 million. A particularly preferred polyethylene oxide comprises a blend of about 40% to 80% of polyethylene oxide having an average molecular weight of about 5 million (e.g. POLYOX COAGULANT) and about 60% to 20% of polyethylene oxide having an average molecular weight of about 300,000 (e.g. POLYOX WSR-N-750). The polyethylene oxide blend may also advantageously contain up to about 10% (for example about 5%) by weight of a low molecular weight (i.e. MW<10,000) polyethylene glycol such as PEG-100.

Suitable PEO/PPO copolymers may have an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the lubricating member in aqueous conditions, especially in combination with a further water soluble polymer (particularly polyethylene oxide), and thus prevent an undesirable feeling in use.

The PEO/PPO copolymer may advantageously be a block copolymer, preferably a tri-block copolymer having the sequence: PEO-PPO-PEO, the later commercially available under tradenames such as Pluracare from BASF and Pluronic from Sigma-Aldrich.

The PEO/PPO copolymer may have a weight ratio of PEO to PPO (i.e. of ethylene oxide repeat units to propylene oxide repeat units), of from 1000:1 to 1:1000 or from 100:1 to 1:100. The PEO/PPO copolymer is typically present at an amount of from 0.01% to 50%, preferably from 0.01% to 50%, more preferably from 2% to 40%, even more preferably from 3% to 25%, even more preferably still from 4% to 20% and most preferably from 5% to 10% by weight of the lubricating material or by weight of the lubricating member.

The lubricating member and or water soluble polymer preferably comprises less than 5%, preferably less than 1% by weight and more preferably is/are substantially free of lathering soaps (i.e. salts of fatty C4 to C30 acids) and lathering surfactants. A lathering surfactant is defined as a surfactant which when combined with water and mechanically agitated, generate a foam or lather. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

Lubricating Material: Silicone Polyether Copolymer

According to the invention, the lubricating material may comprise from about 0.1% to about 70%, preferably from about 1% to about 20%, more preferably from about 1% to 15%, even more preferably from about 1% to about 5% or alternatively from about 40% to about 60%, more preferably from about 45% to about 55%, or alternatively from about 10% to about 60%, preferably from about 20% to about 40% by weight of a silicone polyether copolymer or mixtures thereof.

The silicone polyether copolymer comprises from about 1% to 50%, by weight of polyethylene oxide, from about 20% to about 90% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

While silicone polyether block copolymers are known in the art to provide a number of benefits such as foaming, defoaming, wetting, deaeration and lubricity, it has been now surprisingly found that the selection of silicone block copolymers having from 20% to 90% by weight of polypropylene oxide and from 1% to 50% of polyethylene oxide unexpectedly provide improved lubrication while ensuring the required level of water dispersion and or solubility verses silicone polyether block copolymers having less or no polypropylene oxide and more polyethylene oxide. Moreover, the use of such silicone block copolymers provides improved adhesion to the skin verses alternative materials such as copolymers of polyethylene oxide and polypropylene oxide. Furthermore, the inclusion of 1% to 20% of silicone by weight of the silicone polyether block copolymer surprisingly provides desirable levels of lubrication despite being present at low levels in the polymer.

The copolymers are block copolymers and may preferably have a pendant graft structure. The silicone polyether block copolymer comprises from 1% to 50%, preferably from 10% to 20%, more preferably about 20% by weight of polyethylene oxide. The silicone polyether block copolymer comprises from 20% to 90%, preferably from 40% to 90%, more preferably from 50% to 80%, most preferably about 65% by weight of polypropylene oxide. The silicone polyether block copolymer comprises from 1% to 20%, preferably 10% to 20%, more preferably about 15% by weight of silicone.

The silicone polyether block copolymer preferably has a ratio of polyethylene oxide units to polypropylene oxide units of from 3.0 to 0.1, preferably from 2.0 to 0.1, more preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 19000, more preferably from about 10000 to 15000.

In a preferred embodiment the silicone polyether copolymers suitable for use herein only contain repeating units of silicone, polyethylene oxide and polypropylene oxide. Silicone polyether copolymers comprising additional alkyl chains are preferably excluded.

Suitable silicone polyether copolymers are available from Momentive under the Silwets trademark products including L7210. Preferably the silicone polyether block copolymer is liquid at 25° C., so that it can be provided in a liquid form for spray coating manufacturing methods. The melting point is determined according to ASTM D5440-93. Preferably the silicone polyether block copolymer is sparingly soluble, preferably soluble or more preferably freely soluble in water according to the United States' Pharmacopeia (USP) definition in 31/NF 26 Vol. 2 General Notices, Page Xvii. According to that definition, sparingly soluble means 30 to 1000 parts of water are needed to dissolve 1 part solute, soluble means that 10 to 30 parts of water are needed to dissolve 1 part solute and freely soluble means than from 1 to 10 parts of water are needed to dissolve 1 part of solute.

In one embodiment the lubricating member comprises silicone polyether block copolymer and a water soluble polymer, preferably polyethylene oxide at a weight ratio of from 1:8 to 8:1, preferably from 1:5 to 5:1, more preferably from 1:3 to 3:1 and even more preferably from 1:2 to 2:1.

Lubricating Mmaterial: Optional Hydrophobic Compound

According to the invention the lubricating member may further comprise a hydrophobic compound or mixtures thereof. In one embodiment the lubricating member comprises from 1% to 40%, preferably from 5% to 40%, more preferably from about 10% to about 40%, even preferably from about 12% to about 30% by weight of a hydrophobic compound and/or mixtures thereof. Suitable hydrophobic compounds include natural oils and/or waxes and/or fats; synthetic waxes or oils; triglycerides; skin active agents, sensates, fragrance oils, silicones and mixtures thereof. The hydrophobic material can provide a number of in use benefits such as lubrication, skin feel and cooling sensation.

The hydrophobic compound may comprise skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil, Iso E Super [(1-(1,2,3,4,5,6,7,8-octahydro-2,3,8,8-tetramethyl-2-naphthalenyl)ethanone]; and mixtures thereof.

In some embodiments, the hydrophobic compound comprises one or more sensates. A large number of coolant compounds of natural or synthetic origin are known. The most well known is peppermint oil. Among synthetic coolants, many are derivatives of or are structurally related to menthol, i.e., containing the cyclohexane moiety, and derivatized with functional groups including carboxamide, ketal, ester, ether and alcohol. Non-limiting examples include methyl emthylamido oxalate, (under the tradename Frescolat X-cool available from Symrise), menthyl lactate (such as Frescolate ML Natural available from Symrise), and Menthyl Pyrrolidone Carboxylate also known as Menthyl PCA (under the tradename Questices available from Givaudan).

Hydrophobic compounds may be selected from capric and/or caprylic triglycerides, grape seed oil, olive oil, microcrystalline wax, shea butter, cocoa butter, lanolin, essential oil, peppermint oil, isohexadecane, petrolatum, silicone polymers including waxes and oils (selected from dimethicones, phenylated silicones and mixtures thereof) and mixtures thereof.

Optional Ingredients: Hydrophobic Binders

The lubricating member may also further comprise a water-insoluble material such as hydrophobic binders. Such components may enhance the life of the lubricating material by reducing its tendency to be mechanically eroded. Advantageously, the hydrophobic binder is solid at standard temperature and pressure. Suitable hydrophobic binders include divalent metal cation stearate, preferably magnesium stearate, calcium stearate, zinc stearate, or mixtures thereof, more preferably magnesium separate; ethyl cellulose; polycaprolactone; polyethylene; polypropylene; polystyrene; butadiene-styrene copolymer (e.g. medium and high impact polystyrene); polyacetal; acrylonitrilebutadiene-styrene copolymer; ethylene vinyl acetate copolymer and blends such as polypropylene/polystyrene blend; and mixtures thereof. Preferred water insoluble materials are polyethylene, polypropylene, polystyrene; butadiene-styrene copolymer including medium and high impact polystyrene, polyacetal, acrylonitrilebutadiene-styrene copolymer, ethylene vinyl acetate copolymer and mixtures thereof. The lubricating material may comprise from about 1 to about 50%, preferably from about 10% to about 40% more preferably from about 20% to about 40% by weight of hydrophobic binder. The hydrophobic binder may fall under the definition of hydrophobic compound as used herein and in such a case should be included for purposes of determining the amount by weight of the hydrophobic compound or mixture.

In some embodiments, the lubricating material may comprise any other ingredients commonly found in commercially available shaving aid members. The lubricating member may therefore contain other conventional shaving aid ingredients, such as low molecular weight water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, skin feel/care actives such as water soluble cationic polymers, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials etc and mixture thereof. These ingredients may fall under the definition of hydrophobic compounds as used herein and should be included as such in determining the amounts of hydrophobic compounds.

The lubricating member comprising the combination of water soluble polymer and silicone polyether block copolymer as defined in claim 1 and preferably comprising any optional components present, may have a coefficient of friction as defined according to the method described herein below of 0.0300 or less, preferably of 0.0275 or less, more preferably of 0.0250 or less in order to improve lubrication.

Method of Manufacture/Processing

The lubricating member may be formed using any method known in the art such as injection molding, pressing, impregnation, spray-coating, calendaring and extrusion. All of the components of the lubricating member can be blended prior to molding or extrusion. For best results, it is preferred that the components are dry. In summary, the method comprises the steps of providing a feed comprising the water soluble polymer and silicone polyether block copolymer, and molding, pressing, impregnating, spray-coating, calendaring and/or extruding said feed to form a solid lubricating member. Additional optional steps may be included depending on the process of manufacture which is utilized for example heating said feed to a temperature of from about 120° C. to about 200° C.

For example, the blended components may be extruded through a Haake System 90, ¾ inch diameter extruder with a barrel pressure of about 1000-2000 psi, a rotor speed of about 10 to 50 rpm, and a temperature of about 150°-185° C. and a die temperature of about 170°-185° C. Alternatively, a 1¼ inch single screw extruder may be employed with a processing temperature of 175°-200° C., preferably 185°-190° C., a screw speed of 20 to 50 rpm, preferably 25 to 35 rpm, and an extrusion pressure of 1800 to 5000 psi, preferably 2000 to 3500 psi. The extruded member is air cooled to about 25° C. To injection mold the lubricating member it is preferred to first extrude the powder blend into pellets. This can be done on a 1¼ or 1½ inch single screw extruder at a temperature of 120°-180° C., preferably 140°-150° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 165° to 250° C., preferably from 180° to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

The lubricating member may be manufactured using a hot melt process. In such processes the waxes are melted in a water bath to a temperature of 85° C. stirred until completely melted. The liquid silicone polyether block copolymer is then added and stirred. The temperature is then reduced to about 55° C. when the remaining components are added while stirring. The molten material is then poured into a mold and pressure applied. The member is removed from the mold upon cooling.

In another embodiment, the lubricating member may alternatively be provided in the form of a compressed powder. For such embodiments, the lubricating member may be manufactured whereby the water soluble polymer and other solid dry components are provided as particulates and mixed. The particulate material(s) is solid at 25° C. and preferably has a melting point of 30° C. or more. The lubricating member thus may comprise from 10% to 90% by weight of a particulate material(s) of a water soluble polymer or mixtures thereof.

The silicone polyether block copolymer is, if necessary, liquefied and then spray coated onto at least a portion of the water soluble polymer particulate and other dry components if present. Preferably at least 95%, more preferably at least 98% and even more preferably substantially 100% of the water soluble polymer and preferably any other dry particulate material components present are spray coated with the silicone polyether block copolymer. Hydrophobic compounds if present may also be spray coated as a mixture with the silicone polyether block copolymer or in a separate spray coating step. The resulting mixture is then compression compacted to form a tablet.

The term compression and/or compression molding or compression compaction as used herein refers to a process by which the bulk density of a particulate or powder is reduced to form a solid tablet by the application of pressure. Typically, this is performed without the application of external shear force or heat. Preferably the compression compaction is conducted below the melting point of at least one, preferably all the particulate components, preferably at ambient temperature of 25° C. As such the particulates retain their integrity after the compression process and are typically visible by the naked eye after the compression process is completed.

In certain embodiments, additional energy sources such as heat may be applied during or post compression to increase inter-particulate bonding and increase the rigidity of the resulting lubricating member but which preferably does not result in any substantial melting of the particulate material. Preferably however this method does not require an extrusion or injection molding step or the application of energy sources such as heat.

The lubricating member may thus be provided in the form of a compressed powder from particulates. Preferably the particulates have an average particle size distribution of from about 50 to 1250 microns and preferably from about 300 to 1250 microns, more preferably about 1000 microns. Alternatively, the particulate size is such that 90% of particles pass through a 20 mesh screen; i.e. 90% of particles are less than 841 micron in diameter. The lubricating member is compressed preferably directly into a preform or container with a compression force of typically greater than 1 KN. This may be achieved using any method and equipment known in the art such as a die press. The bulk density of the particulate material prior to compression is typically about 300 to 600 kg/m$^3$ and increases to about 1000 to 1200 kg/m$^3$ following compression. Bulk density thus may be increased by about 200% to about 400% after the compression. While not bound by theory, it has been found that the use of particulate compression manufacturing, preferably cold particulate compression (i.e. at 25° C. or less) to form the lubricating member enables highly lubricous components to be incorporated therein while not negatively impacting the water solubility and swelling performance of the water soluble polymer. This also allows flexibility in the size of the resulting lubricating member to be used for multiple razor cartridges while enabling the effective delivery of the silicone polymer to the skin of the consumer in use.

Hair Removal Head

According to some embodiments of the invention, the lubricating member finds particular application for hair removal devices. Hair removal devices generally comprise a hair removal head and a handle or grip portion, upon which the hair removal head is mounted. The hair removal device can be manual or power driven and can be used for wet and/or dry application. The hair removal head can include a wide scraping surface such as where the hair removal device is used with a depilatory, or be a razor cartridge or foil where the device is a shaving razor. The hair removal head may be replaceable and/or pivotally connected to a cartridge connecting structure and in turn or independently (e.g. permanently fixed) to a handle. In some embodiments, the cartridge connecting structure includes at least one arm to releasably engage the hair removal head.

The hair removal head typically comprises one or more elongated edges usually positioned between a first and second end, said one or more elongated edges comprising a tip extending towards said first end. Where the hair removal head is a razor cartridge the one or more elongated edges can include blades. For example, U.S. Pat. No. 7,168,173 generally describes a Fusion® razor that is commercially available from The Gillette Company and which includes a razor cartridge with multiple blades. Additionally, the razor cartridge may include a guard as well as a skin engaging member. A variety of razor cartridges can be used in accordance with the present invention. Non limiting examples of suitable razor cartridges, with and without fins, guards, and/or shave aids, include those marketed by The Gillette Company under the Fusion®, Venus® product lines as well as those disclosed in U.S. Pat. Nos. 7,197,825; 6,449,849; 6,442,839; 6,301,785; 6,298,558; 6,161,288; and U.S. Patent Publ. 2008/060201. Those skilled in the art will understand that the lubricating member can be used with any currently marketed system or disposable razor, including those having 2, 3, 4 or 5 blades. In such a case, the hair removal device is a razor, the hair removal head is a razor cartridge and the one or more elongated edges are blades. Another example of a hair removal device is a scraping tool for use with a hair removal composition, i.e. a depilatory.

In some embodiments, said at least one lubricating member is located on the portion of the cartridge that contacts skin during the hair removal process, forward and/or aft of the blades. A feature "forward" of the one or more elongated edges, for example, is positioned so that the surface to be treated by the hair removal device encounters the feature before it encounters the elongated edges. A feature "aft" of the elongated edge is positioned so that the surface to be treated by the hair removal device encounters the feature after it encounters the elongated edges. Where more than one lubricating member is provided on the hair removal device, they can be the same (identical) or different, in terms of physical shape/structure and/or chemical composition, and one or more of them may comprise the spray coated particulate.

In some particular embodiments, a plurality (e.g. 2, a first and second) of lubricating members may be provided on the hair removal head, with the first skin engaging member comprising the same composition or different. These lubricating members may be placed collectively (for example adjacent to one another) ahead of or behind the elongated edges (e.g. blades on a razor cartridge), including side by side, or separately with one ahead of the elongated edges and the other behind.

The lubricating member may be free standing utilizing a suitable attachment means such as adhesive or may be contained at least partially within a container.

The container typically has a base and at least one side wall extending vertically preferably perpendicular from said base and a skin contacting surface. In a preferred embodiment said container comprises a base and at least 2 side walls, more preferably at least 4 side walls, preferably said walls completely enclosing the base. Typically, each pair of walls are substantially parallel and preferably one pair of walls is substantially parallel to the at least two blades. Alternatively, the base may be enclosed by a one piece single wall. The container may form any shape including substantially rectangular, or oval. The container typically has a front wall adjacent the blades and a rear wall, preferably substantially parallel thereto and furthest from said blades.

The container is preferably further provided with at least one dispensing orifice for dispensing the lubricating member onto the skin during use. In one embodiment the container is provided with a top extending substantially perpendicular from the side wall (s). The container would in such an embodiment typically have a receiving region for receiving the lubricating member. The top may be substantially parallel to the base or it may be at an angle such that the distance of the top from the blade plane increases or decreases as the distance of the container from the blades increases. In one embodiment the height of the top of the container increases in distance from the blade plane as the container distance from the blades increases. In an alternative embodiment the height of the top of the container decreases in distance from the blade plane as the container distance from the blade increases.

The orifice may be of any shape and may, for example, have a cross sectional area of from about 0.00324 to about 1.613 $cm^2$. Small orifices can also be provided with a cross sectional area of from about 0.0324 to about 0.324 $cm^2$, or from about 0.0645 to about 0.16135 $cm^2$. Larger orifices can have cross sectional areas of from about 0.324 to about 1.613 $cm^2$, or from about 0.645 to about 1.29 $cm^2$. The container may comprise a single orifice or multiple orifices which may be large and/or small. In one embodiment the container comprises at least two orifices. Combinations of small and large orifices can also be provided on the same skin engaging member, or on separate members on the same cartridge, depending on the desired dispense rate and amount of exposure of the lubricating material to water. In one embodiment the top of the container is provide with one preferably two orifices, more preferably two substantially identical orifices adjacent one another.

The skin engaging surface of the container which has a surface area, while the at least one orifice (i.e. the sum for all orifices if a plurality are present) has a cross sectional area such that the surface area and cross sectional area are in a ratio of from about 50:1 to about 1:1, or about 25:1 to about 2:1, or about 10:1 to about 3:1.

In some embodiments, at least a portion of said container is not linear for example angled or curvilinear. Curvilinear as defined herein means that at least a portion is curved such that it does not form a straight line. Where at least two containers are provided, they can also be positioned relative to one another such that they do not form a straight line. Alternatively, the curved or angled nature is such that it forms at least a partial ring. A partial ring, as defined herein, means that the structure has at least two curved or angled sections which are concave to form an inner region. The partial ring can also include a curved or angled portion which is positioned convex to said inner region. One or more of said containers may also be positioned relative to one another to form a full ring.

The container can be formed of a variety of materials. The container may, preferably be for example, provided from a non-water soluble material such that it does not degrade or dissolve during normal use.

The container typically has sufficient mechanical strength and rigidity to provide adequate mechanical strength to the entire skin engaging member, both as initially produced and after a significant amount of lubricating material has leached out of the container. Alternatively, or in addition a further reinforcing member may also be utilized. In some embodiments, the container comprises a base and one or more side walls, forming a receiving region, or channel, onto or into which the lubricating material is placed.

The side walls may or may not be the same height (as measured extending away from the base of the container). At least one of the side walls can have a height of about 0.1 cm to about 1 cm, preferably from about 0.2 cm to about 0.4 cm. The pair of side walls can be biased away from each other as the walls extend away from said base, or they can be biased towards each other. At least one wall extends vertically from the base and is preferably perpendicular to the blade plane (P). One or both ends of the container can be enclosed, e.g. as described in U.S. Pat. No. 7,581,318. The term maximum height of at least one wall as used herein refers to the first front wall preferably substantially parallel to the at least two blades and closest thereto or it refers to the rear wall farthest from said at least two blades. In one embodiment the said at least one wall is closest to said at least two blades. In an alternative embodiment the at least one wall is farthest from said at least two walls. In one embodiment, the ratio of the height of the front wall to the rear wall is from 5:1 to 1:5, more preferably from 2:1 to 1:2 and more preferably the height of the front wall is greater than the rear wall. The walls have a thickness of from 0.1 cm to 1.0 cm, preferably from 0.3 to 0.5 cm.

The container may be made of a water-insoluble polymer, particularly a thermoplastic resin. Thermoplastic resins are those materials which can be extruded or molded into a shape and are resilient under normal environmental conditions such as contact with water, even up to normal household hot water temperatures (for example up to 125° C.); normal wear and tear by consumers during use; device assembly and shipping, etc. Thermoplastic resins suitable for use in the carrier include polystyrene, high impact polystyrene (polystyrene-butadiene), polypropylene, filled polypropylene, polyethylene, nylon ethylene vinyl acetate, and blends such as 70% nylon/30% polyethylene oxide, 60% polystyrene/40% polyethylene oxide butadiene styrene copolymer, polyacetal, acrylonitrile-butadiene styrene copolymer, and mixtures thereof. The preferred resins are high impact polystyrene, polystyrene, ethylene vinyl acetate (EVA), and mixtures thereof.

In some embodiments, the cartridge comprises a guard comprising at least one elongated flexible protrusion to engage a user's skin. The at least one flexible protrusion may comprise flexible fins generally parallel to said one or more elongated edges. Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695 A1 (disclosing an elastomeric guard having a guard forming at least one passage extending between an upper surface and a lower surface). In some embodiments, said lubricating member is positioned on the cartridge aft of the guard and forward of said elongated edge. In another embodiment, the lubricating member is positioned on the cartridge forward of the guard. This embodiment can be particularly useful to deliver the lubricating member prior to contact with the guard.

Test Methods

Molecular Weight Distribution

The weight average molecular weight (Mw) is measured using gel permeation chromatography (GPC) and multi-angle laser light scattering (MALLS). The GPC/MALLS system used for the analysis is comprised of a Waters Alliance e2695 Separations Module, a Waters 2414 interferometric refractometer, and a Wyatt Heleos II 18 angle laser light scattering detector. The column set used for separation is purchased from TOSOH Biosciences LLC, King of Prussia, Pa. and included: Guard Column TSKgel G1000Hx-GMHx1-L (Cat #07113), TSKgel G3000Hx1 (Cat #0016136), TSKgel G2500Hx1 (Cat #0016135), and TSKgel G2000Hx1 (Cat #0016134). Wyatt ASTRA 6 software was used for instrument operation and data analysis. The 90° light scattering detection angle is calibrated using filtered, anhydrous toluene. The remaining detection angles are normalized using an isotropic scatterer in THF. To verify instrument performance of the MALLS and RI (refractive index) detectors, a poly(styrene) standard with a known Mw and known dn/dc (in the mobile phase) is run. Acceptable performance of the MALLS and RI detectors gives a calculated Mw within 5% of the reported Mw of the poly (styrene) standard and a mass recovery between 95 and 105%.

To complete the GPC/MALLS analysis, a value of dn/dc is needed. The value of dn/dc is measured as follows. The RI detector is thermostated to 35 degrees Celsius. A series of five concentration standards of the metathesized unsaturated polyol ester in THF is prepared in the range 0.5 mg/ml to 5.5 mg/ml. A THF blank is injected directly into the refractive index detector, followed by each of the metathesized unsaturated polyol ester concentration standards, and ending with another THF blank. The volume of each sample injected is large enough to obtain a flat plateau region of constant differential refractive index versus time; a value of 1.0 ml is typically used. In the ASTRA software, a baseline is constructed from the initial and final THF injections. For each sample, peak limits are defined and the concentrations entered to calculate dn/dc in the ASTRA software. For the metathesized canola oil of Example 2 in THF, a dn/dc value of 0.072 ml/g is obtained.

For the GPC/MALLS analysis of a metathesized unsaturated polyol ester, a total of three samples are evaluated: the metathesized unsaturated polyol ester, a non-metathesized unsaturated polyol ester (glycerol trioleate [122-32-7], Sigma-Aldrich, Milwaukee, Wis.), and a representative olefin (1-octadecene, [112-88-9], Sigma-Aldrich, Milwaukee, Wis.). The GPC samples are dissolved in tetrahydrofuran (THF). Concentrations for the metathesized unsaturated polyol ester are approximately 20 mg/ml, and concentrations for the non-metathesized unsaturated polyol ester and olefin are approximately 5 mg/ml. After all the material is dissolved, each solution is filtered by a 0.45 micron nylon filter disk into a GPC autosampler vial for analysis. The GPC column temperature is at room temperature, approximately 25 degrees Celsius. HPLC grade THF is used as the mobile phase and is delivered at a constant flow rate of 1.0 ml/min. The injection volume is 100 microliters and the run time is 40 minutes. Baselines are constructed for all signals. Peak elution limits include metathesized unsaturated polyol ester and non-metathesized unsaturated polyol ester, but exclude later eluting residual olefin. The retention times of the non-metathesized unsaturated polyol ester and olefin were determined from the separate injection runs of both the non-metathesized unsaturated polyol ester and olefin. Baselines and scattering detectors are reviewed.

Oligomer Index

The oligomer index of the metathesized unsaturated polyol ester is calculated from data that is determined by Supercritical Fluid Chromatography-Fourier Transform Orbital Trapping Mass Spectrometry (SFC-Orbitrap MS). The sample to be analyzed is typically dissolved in methylene chloride or a methylene chloride—hexane mixture at a concentration of 1000 ppm (1 mg/mL). A further 25×-100× dilution is typically made into hexane (for a final concentration of 10-40 ppm). A volume of 2-7.5 µL is typically injected on to a SFC column (for example, a commercially available 3 mm i.d.×150 mm Ethylpyridine column, 3 µM particle size).

During the chromatography run, the mobile phase is typically programmed from 100% carbon dioxide with a gradient of one percent per minute methanol. The effluent from the column is directed to a mixing tee where an ionization solution is added. The ionization medium is typically 20 mM ammonium formate in methanol at a flow of 0.7 mL/min while the SFC flow is typically 1.6 mL/min into the tee. The effluent from the mixing tee enters the ionization source of the Orbitrap Mass Spectrometer, which is operated in the heated electrospray ionization mode at 320° C. In one aspect, a hybrid linear ion trap—Orbitrap mass spectrometer (i.e., the Orbitrap Elite from Thermoelectron Corp.) is calibrated and tuned according to the manufacturer's guidelines. A mass resolution (m/Δm peak width at half height) from 100,000 to 250,000 is typically used. C,H,O compositions of eluting species (typically associated with various cations, e.g., $NH_4^+$, $H_4^+$, $Na^+$) are obtained by accurate mass measurement (0.1-2 ppm) and are correlated to metathesis products. Also, sub-structures may be probed by linear ion trap "MS" experiments with subsequent accurate-mass analysis in the Orbitrap, as practiced typically in the art.

The metathesis monomers, dimers, trimers, tetramers, pentamers, and higher order oligomers are fully separated by SFC. The chromatogram based on ion current from the Orbitrap MS may be integrated, as typically practiced in the art, for each of the particular oligomer groups including metathesis monomers, metathesis dimers, metathesis trimers, metathesis pentamers, and each of the higher order oligomers. These raw areas may then be formulated into various relative expressions, based on normalization to 100%. The sum of the areas of metathesis trimers through the highest oligomer detected is divided by the sum of all metathesis species detected (metathesis monomers to the highest oligomer detected). This ratio is called the oligomer index. As used herein, the "oligomer index" is a relative measure of the fraction of the metathesized unsaturated polyol ester which is comprised of trimers, tetramers, pentamers, and higher order oligomers.

Iodine Value

Another aspect of the invention provides a method to measure the iodine value of the metathesized unsaturated polyol ester. The iodine value is determined using AOCS Official Method Cd 1-25 with the following modifications: carbon tetrachloride solvent is replaced with chloroform (25 ml), an accuracy check sample (oleic acid 99%, Sigma-Aldrich; IV=89.86±2.00 cg/g) is added to the sample set, and the reported IV is corrected for minor contribution from olefins identified when determining the free hydrocarbon content of the metathesized unsaturated polyol ester.

Free Hydrocarbon Content

Another aspect of this invention provides a method to determine the free hydrocarbon content of the metathesized unsaturated polyol ester. The method combines gas chromatography/mass spectroscopy (GC/MS) to confirm identity of the free hydrocarbon homologs and gas chromatography with flame ionization detection (GC/FID) to quantify the free hydrocarbon present.

Sample Prep: The sample to be analyzed was typically trans-esterified by diluting (e.g. 400:1) in methanolic KOH (e.g. 0.1N) and heating in a closed container until the reaction was complete (i.e. 90° C. for 30 min.) then cooled to room temperature. The sample solution could then be treated with 15% boron tri-fluoride in methanol and again heated in a closed vessel until the reaction was complete (i.e. at 60° C. for 30 min.) both to acidify (methyl orange—red) and to methylate any free acid present in the sample. After allowing to cool to room temperature, the reaction was quenched by addition of saturated NaCl in water. An organic extraction solvent such as cyclohexane containing a known level internal standard (e.g. 150 ppm dimethyl adipate) was then added to the vial and mixed well. After the layers separated, a portion of the organic phase was transferred to a vial suitable for injection to the gas chromatograph. This sample extraction solution was analyzed by GC/MS to confirm identification of peaks matching hydrocarbon retention times by comparing to reference spectra and then by GC/FID to calculate concentration of hydrocarbons by comparison to standard FID response factors.

A hydrocarbon standard of known concentrations, such as 50 ppm each, of typically observed hydrocarbon compounds (i.e. 1-dodecene, 1-tridecene, 1-tetradecene, 1-pentadecene, 1-hexadecene, 1-heptadecene, 1-octadecene, dodecane, tridecane, tetradecane, pentadecane, hexadecane, heptadecane and octadecane) was prepared by dilution in the same solvent containing internal standard as was used to extract the sample reaction mixture. This hydrocarbon standard was analyzed by GC/MS to generate retention times and reference spectra and then by GC/FID to generate retention times and response factors.

GC/MS: An Agilent 7890 GC equipped with a split/splitless injection port coupled with a Waters QuattroMicroGC mass spectrometer set up in EI+ ionization mode was used to carry out qualitative identification of peaks observed. A non-polar DB1-HT column (15 m×0.25 mm×0.1 um df) was installed with 1.4 mL/min helium carrier gas. In separate runs, 1 uL of the hydrocarbon standard and sample extract solution were injected to a 300° injection port with a split ratio of 25:1. The oven was held at 40° C. for 1 minute then ramped 15° C./minute to a final temperature of 325° C. which was held for 10 minutes resulting in a total run time of 30 minutes. The transfer line was kept at 330° C. and the temperature of the EI source was 230° C. The ionization energy was set at 70 eV and the scan range was 35-550 m/z.

GC/FID: An Agilent 7890 GC equipped with a split/splitless injection port and a flame ionization detector was used for quantitative analyses. A non-polar DB1-HT column (5 m×0.25 mm×0.1 um df) was installed with 1.4 mL/min helium carrier gas. In separate runs, 1 uL of the hydrocarbon standard and sample extract solution was injected to a 330° injection port with a split ratio of 100:1. The oven was held at 40° C. for 0.5 minutes then ramped at 40° C./minute to a final temperature of 380° C. which was held for 3 minutes resulting in a total run time of 12 minutes. The FID was kept at 380° C. with 40 mL/minute hydrogen gas flow and 450 mL/min air flow. Make up gas was helium at 25 mL/min.

The hydrocarbon standard was used to create a calibration table in the Chemstation Data Analysis software including known concentrations to generate response factors. These response factors were applied to the corresponding peaks in the sample chromatogram to calculate total amount of free hydrocarbon found in each sample.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Non-limiting examples of product formulations disclosed in the present specification are summarized below.

Example 1

Synthesis of Metathesized Canola Oil

Prior to the metathesis reaction, the RBD (refined, bleached, and deodorized) canola oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of Celite® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of Celite® 545 diatomaceous earth. The oil is treated a second time with 2% bleaching clay (Filtrol F-160, BASF, Florham Park, N.J.) for ~6 hours. The oil is filtered through a bed of Celite® 545 diatomaceous earth and then rotary evaporated to concentrate.

The metathesized canola oil is then passed through a wipe film evaporator at 180° C. and <0.5 Torr vacuum to remove olefins up to and including C-18 chain lengths. Representative examples are summarized in the table below.

| Example | Pretreated Canola Oil (g)[a] | Catalyst | Catalyst (g) | Max Temperature (° C.) | Max Vacuum (Torr) |
|---|---|---|---|---|---|
| 1A | 500 | 1[b] | 0.25 | 61 | 7.9 |
| 1B | 500 | 2[c] | 0.25 | 62 | 0.6 |

[a]Canola oil from J. Edwards, Braintree, MA.
[b]Tricyclohexylphosphine [4,5-dimethyl-1,3-bis(2,4,6-trimethylphenyl)imidazol-2-ylidene][2-thienylmethylene]ruthenium (II) dichloride [1190427-50-9] available as CatMETium RF-3 from Evonik Corporation, Parsippany, NJ.
[c]Tricyclohexylphosphine [1,3-bis(2,4,6-trimethylphenyl)imidazol-2-ylidene][2-thienylmethylene] ruthenium(II) dichloride [1190427-49-6] available as CatMETium RF-2 from Evonik Corporation, Parsippany, NJ.

The samples 1A and 1B are analyzed for weight average molecular weight, iodine value, free hydrocarbon content and oligomer index, using methods described previously, and are found to approximately have the following values:

| Example | Mw (g/mol) | Iodine Value (cg/g) | Free Hydrocarbon content (wt %) | Oligomer Index |
|---|---|---|---|---|
| 1A | 5,400 | 85 | 0.5 | 0.05 |
| 1B | 3,900 | 85 | 0.5 | 0.04 |

Example 2

Remetathesis of Metathesized Unsaturated Polyol Ester

Metathesized canola oil, sufficiently stripped of residual olefins (176.28 g from Example 1A) is blended with pre-treated canola oil (350.96 g, pretreated as described in Example 1) in a round-bottomed flask. The blend is sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of Celite® 545 diatomaceous earth. The oil is treated a second time with 2% bleaching clay (Filtrol F-160, BASF, Florham Park, N.J.) for ~6 hours. The oil is filtered through a bed of Celite® 545 diatomaceous earth and then rotary evaporated to concentrate.

The remetathesized canola oil is then passed through a wipe film evaporator at 180° C. and <0.5 Torr vacuum to remove olefins up to and including C-18 chain lengths. A representative example is summarized in the table below.

| Example | Oil Blend (g) | Catalyst[a] (g) | Max Temperature (° C.) | Max Vacuum (Torr) |
|---|---|---|---|---|
| 2 | 500 | 0.27 | 65 | 0.2 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.

The sample 2 is analyzed for weight average molecular weight, iodine value, free hydrocarbon content and oligomer index, using methods described previously, and is found to approximately have the following values:

| Example | Mw (g/mol) | Iodine Value (cg/g) | Free Hydrocarbon content (wt %) | Oligomer Index |
|---|---|---|---|---|
| 2 | 13,000 | 80 | 0.5 | 0.07 |

Example 3

Synthesis of Metathesized Unsaturated Polyol Esters

Prior to the metathesis reaction, the RBD (refined, bleached, and deodorized) oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of Celite® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized oil is diluted in hexanes ([110-54-3], EMD, Billerica, Mass.). To the diluted material, 2% bleaching clay (Filtrol F-160, BASF, Florham Park, N.J.) is added and mixed for ~6 hours. The metathesized oil is filtered through a bed of Celite® 545 diatomaceous earth. The metathesized oil is treated a second time with 2% bleaching clay (Filtrol F-160, BASF, Florham Park, N.J.) for ~6 hours. The metathesized oil is filtered through a bed of Celite® 545 diatomaceous earth and then rotary evaporated to concentrate.

The metathesized unsaturated polyol ester is then passed through a wipe film evaporator at 180° C. and <0.5 Torr vacuum to remove olefins up to and including C-18 chain lengths. Representative examples are summarized in the table below.

| Example | Starting unsaturated polyol ester | Pretreated Oil (g) | Catalyst[a] (g) | Max Temperature (° C.) | Max Vacuum (Torr) |
|---|---|---|---|---|---|
| 3A | High erucic acid rapeseed oil | 500 | 0.25 | 61 | 7.9 |
| 3B | Blend of High erucic acid rapeseed oil and canola oil, 50/50 by weight | 500 (250 g HEAR oil and 250 g canola oil) | 0.25 | 61 | 7.9 |
| 3C | High oleic soybean oil | 500 | 0.25 | 61 | 7.9 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as Cat-METium RF-3 from Evonik Corporation, Parsippany, NJ.

Example 4

Hydrogenations are performed in a T316 stainless steel, 600 ml Parr reactor (Model Number 4563) containing internal cooling coils and a stir shaft with 2 impellers comprised of 4 blades each.

The metathesized unsaturated polyol ester (approximately 200 g) is dissolved in hexanes (120 ml, [110-54-3], EMD, Billerica Mass.). To this solution is added a slurry of Nickel on Silica (20 g, [7440-02-0], Catalog #28-1900, Strem Chemicals, Inc., Newburyport, Mass.). The slurried mixtures is transferred via vacuum to the Parr reactor. The mixture is degassed with several vacuum/nitrogen fill cycles. Then with stirring (800-900 rpm), hydrogen gas (550-650 psig, [1333-74-0], UHP grade, Wright Brothers, Inc., Montgomery, Ohio) is charged to the reactor. The reaction is heated at 150° C. and hydrogen gas pressure reduction monitored until constant (~12 hours).

The reaction is cooled to 60° C. and drained from the reactor. The reactor is rinsed with methyl tert-butyl ether ([1634-04-4], EMD, Billerica, Mass.) and combined with the solid hydrogenated metathesized polyol ester. A hot filtration is then performed to remove the catalyst, followed by a vacuum to remove all residual solvent. Fully hydrogenated materials are obtained using the method above. Lower hydrogenation levels are obtained by decreasing the reaction temperature to 125 degrees Celsius using 5 grams of catalyst and reducing the reaction time and hydrogen consumed. Iodine Value (IV) is measured, as described elsewhere.

Example 5

The metathesis monomers, dimers, trimers, tetramers, pentamers, and higher order oligomers from the product in Example 2 are fully separated by SFC using the method described above. The individual SFC fractions are collected and trimers, tetramers, and higher order oligomers are combined. The oligomer index of this sample is about 1.

Exemplified Compositions: Formulation Examples

| Ingredient | Example 1 (% w/w) | Example 2 (% w/w) | Example 3 (% w/w) |
|---|---|---|---|
| Polyox WSR coag | — | 10 | 20 |
| Polyox N60k | 30 | — | — |
| Silwet L7210 * | 10 | 45 | 20 |
| Metathesized unsaturated polyol ester | 10 | 5 | 10 |
| Softcat SL5 ** | — | — | 10 |
| Nhance 3196 *** | — | 10 | — |
| Petrolatum | — | — | 10 |
| DC200, 350 cst $ | 20 | — | — |
| Cetyl alcohol | 30 | 25 | 25 |
| Multiwax 180 MH # | — | 5 | 5 |
| Total | 100 | 100 | 100 |

Suppliers: * Momentive,  Dow Chemicals, * Ashland, $ Dow Corning, # Sonneborn Formulation Examples 1-3 were prepared as follows:
1. Sanitize all equipment.
2. Turn on water bath/vessel jacket to 85° C.
3. Add waxy phase ingredients (cetyl alcohol, multiwax 180 MH) and stir with overhead stirrer until completely melted.
4. Add oil phase ingredients (petrolatum, DC200, Silwet L7210, Metathesized unsaturated polyol ester) and mix until fully liquid.
5. Reduce heat to 55° C. and add powder ingredients (polyox (WSR or N60K), Nhance 3196 and Softcat SL5) until fully dispersed.
6. Pour mixture into a mold
7. Assemble part onto razor cartridge.

I. Formulation Examples

| Ingredients | Example 4 (% w/w) | Example 5 (% w/w) |
|---|---|---|
| Polyox WSR coag | 98.0 | — |
| Polyox N60k | — | 88.0 |

-continued

| Ingredients | Example 4 (% w/w) | Example 5 (% w/w) |
|---|---|---|
| Metathesized unsaturated polyol ester | 2.0 | 2.0 |
| Pluronic F127 * | — | 10.0 |
| Total | 100 | 100 |

Suppliers: * BASF

The lubricating members were prepared by dry mixing the dry ingredients in the table above and then spray coating the metathesized unsaturated polyol ester onto the powder blend. An appropriate amount of the resulting mix was then compressed and compacted into a suitable container for attachment to a razor cartridge, using a die press at 2.2 KN for about 5 seconds.

II. Formulation Examples

| Ingredient | Ex. 6 (% w/w) | Ex. 7 (% w/w) |
|---|---|---|
| Sodium Stearate | 25.4 | 26.2 |
| Propylene Glycol | 14.2 | 13.5 |
| Glycerin | 12.4 | 12.4 |
| Aqua | 12.0 | 12.0 |
| Sorbitol | 6.8 | 6.8 |
| Sodium Laureth Sulfate | 6.8 | 6.8 |
| Sodium Myristate | 4.8 | 4.8 |
| Squalane | 2.2 | 2.2 |
| Olea Europaea (Olive) Fruit Oil | 1.6 | 2.0 |
| Persea Gratissima (Avocado) Oil | 1.6 | 2.0 |
| Metathesized unsaturated polyol ester | 1.3 | 1.3 |
| Polyethylene * | 1.3 | 1.3 |
| Polybutene ** | 1.3 | 1.3 |
| PEG-90M | 1.2 | 1.2 |
| PEG-45M | 1.2 | 1.2 |
| Silwet L7210 | 1.0 | 1.0 |
| Lauryl Dimethicone/Polyglycerin-3 Crosspolymer *** | 1.1 | 1.1 |
| Garcinia Indica Seed Butter | 0.8 | 1.0 |
| Parfum | 1.0 | 1.0 |
| PEG-7M | 0.6 | 0.6 |
| Stearic acid | 0.4 | 0.3 |
| Total | 100.0 | 100.0 |

* Suppliers:  Sensient, * Shin-Etsu

The above ingredients for examples 6 and 7 including the Metathesized unsaturated polyol ester can be formed into a lubricating member according to the methods of making the molded shaving aid composition described in U.S. Pat. No. 7,811,553 paragraphs [0059-0081], in either the poured soap base or process sensitive phase, as well as within a one-step batch process, or a continuous process. It is preferred to incorporate the polyethylene glycols into the process sensitive phase to minimize degradation.

III. Formulation Examples

| Ingredient | Ex. 1 (% w/w) | Ex. 2 (% w/w) | Ex. 3 (% w/w) |
|---|---|---|---|
| HIPS Ineos 5410 | 26.50 | — | 30.00 |
| Elvax 660 | — | 26.50 | — |
| Polyox WSR Coagulant | 33.56 | 33.56 | 38.75 |
| Polyox N750 | 22.69 | 22.69 | 25.00 |
| PCL CAPA 6506 | 5.00 | 5.00 | — |
| Colourant | 4.00 | 4.00 | 1.00 |

-continued

| Ingredient | Ex. 1 (% w/w) | Ex. 2 (% w/w) | Ex. 3 (% w/w) |
|---|---|---|---|
| Irganox Antiox B-215 | 0.25 | 0.25 | 0.25 |
| Metathesized unsaturated polyol ester | 3.00 | 3.00 | 3.00 |
| PEG 4600 | 5.00 | 5.00 | 5.00 |

Example 1

The lubricating members were prepared by dry mixing the dry ingredients in the table above and then spray coating the Metathesized unsaturated polyol ester onto the powder blend. The blended components may be extruded through a Rondol 18, 18 mm diameter extruder with a barrel pressure of about 1000-2000 psi, a rotor speed of about 10 to 50 rpm, and a temperature of about 150° C.-185° C. and a die temperature of about 170° C.-185° C. Alternatively, a 1½ inch single screw extruder may be employed with a processing temperature of 175°-200° C., preferably 185° C.-190° C., a 30 screw speed of 20 to 50 rpm, preferably 25 to 35 rpm, and an extrusion pressure of 1800 to 5000 psi, preferably 2000 to 3500 psi. The extruded strip is air cooled to about 25° C. To injection mold the strips it is preferred to first extrude the powder blend into pellets. This can be done on a 1¼ or 1½ inch single screw extruder at a temperature of 120° C.-180° C., preferably 140° C.-150° C., with a screw speed of 20 to 100 rpm, preferably 45 to 70 rpm. The pellets are then molded in either a single material molding or multi-material molding machine, which may be single cavity or multicavity, optionally equipped with a hot-runner system. The process temperature can be from 165° C. to 250° C., preferably from 180° C. to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

Example 2

The lubricating members were prepared by dry mixing the dry ingredients in the table above and then spray coating the Metathesized unsaturated polyol ester onto the powder blend. The blended components may be extruded through a Rondol 18, 18 mm diameter extruder with a barrel pressure of about 500-1000 psi, a rotor speed of about 10 to 50 rpm, and a temperature of about 100°-160° C. and a die temperature of about 100° C.-160° C. Alternatively, a 1½ inch single screw extruder may be employed with a processing temperature of 100° C.-160° C., preferably 110-130° C., a screw speed of 20 to 50 rpm, preferably 25 to 35 rpm, and an extrusion pressure of 1800 to 7500 psi, preferably 4000 to 6500 psi. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° C. to 185° C., preferably from 110° C. to 145° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature.

Example 3

The lubricating members were made according to example 1 except that Metathesized unsaturated polyol ester is added after formation of the lubricating member. The lubricating members are loaded into a low shear paddle mixer with the mixer running at sufficient speed to create a fluidized zone, Metathesized unsaturated polyol ester was introduced into the mixing zone over 20 seconds, with continued mixing for an additional 10 seconds after Metathesized unsaturated polyol ester addition was complete. Alternatively, the lubricating member may be coated continuously via direct application (immersion, spray) or transfer from an applicator (roller, pad, etc.) to the surface of the member during extrusion and/or at product assembly.

As used herein, molecular weights (mol. wt.s.) are provided in unified atomic mass units, Daltons, or g/mol. It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. Similarly, it should be understood that each feature of the specified embodiment of the invention may be independently applied to each other specified embodiment, as if all such combinations were expressly written herein, unless these combinations are specifically excluded or the relevant features are innately incompatible (e.g. the features are directly contradictory).

All parts, ratios, and percentages herein, in the Description, Examples, and Claims, are by weight of the lubricating member and all numerical limits are used with the normal degree of accuracy afforded by the art, unless otherwise specified.

Combinations:

An example is below:
A. A lubricating member for use on a hair removal device, said lubricating member comprising a lubricating material comprising a) from 1% to 99% by weight of methathesized unsaturated polyol ester methathesized unsaturated polyol ester,
having one or more of the following properties:
(i) a weight average molecular weight of from about 5,000 Daltons to about 50,000 Daltons;
(ii) an oligomer index from greater than 0 to 1; and
(iii) an iodine value of from about 30 to about 200.
B. A device according to Paragraph A, wherein said metathesized unsaturated polyol ester has a weight average molecular weight of from about 5,000 Daltons to about 50,000 Daltons.
C. A device according to Paragraph A wherein said metathesized unsaturated polyol ester has an iodine value of from about 30 to about 200.
D. A lubricating member for use on a hair removal device, said lubricating member comprising a lubricating material comprising a) from 1% to 99% by weight of composition comprising:
a) a metathesized unsaturated polyol ester, said metathesized unsaturated polyol ester having a weight average molecular weight of from about 2,000 Daltons to about 50,000 Daltons; and one or more of the following properties:
(i) a free hydrocarbon content, based on total weight of metathesized unsaturated polyol ester of from about 0% to about 5%;
(ii) an oligomer index from greater than 0 to 1; and
(iii) an iodine value of from about 8 to about 200.
E. A lubricating member according to Paragraph D, wherein said metathesized unsaturated polyol ester has an iodine value of from about 10 to about 200.
F. A lubricating member according to Paragraph D, wherein said metathesized unsaturated polyol ester has an oligomer index from about 0.001 to 1.
G. A lubricating member according to Paragraph A, wherein said metathesized unsaturated polyol ester has a free hydrocarbon content, based on total weight of metathesized unsaturated polyol ester, of from about 0% to about 5%.
H. A lubricating member according to Paragraph A, said composition comprising, based on total composition weight, from about 0.1% to about 50% of said metathesized unsaturated polyol ester.
I. A lubricating member according to Paragraph A, wherein the metathesized unsaturated polyol ester is metathesized at least once.
J. A lubricating member according to Paragraph A, wherein said metathesized unsaturated polyol ester is derived from a natural polyol ester and/or a synthetic polyol ester, preferably said natural polyol ester is selected from the group consisting of a vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, preferably, sucrose, and mixtures thereof.
K. A lubricating member according to Paragraph A, wherein said metathesized unsaturated polyol ester is selected from the group consisting of metathesized Abyssinian oil, metathesized Almond Oil, metathesized Apricot Oil, metathesized Apricot Kernel oil, metathesized Argan oil, metathesized Avocado Oil, metathesized Babassu Oil, metathesized Baobab Oil, metathesized Black Cumin Oil, metathesized Black Currant Oil, metathesized Borage Oil, metathesized Camelina oil, metathesized Carinata oil, metathesized Canola oil, metathesized Castor oil, metathesized Cherry Kernel Oil, metathesized Coconut oil, metathesized Corn oil, metathesized Cottonseed oil, metathesized Echium Oil, metathesized Evening Primrose Oil, metathesized Flax Seed Oil, metathesized Grape Seed Oil, metathesized Grapefruit Seed Oil, metathesized Hazelnut Oil, metathesized Hemp Seed Oil, metathesized Jatropha oil, metathesized Jojoba Oil, metathesized Kukui Nut Oil, metathesized Linseed Oil, metathesized Macadamia Nut Oil, metathesized Meadowfoam Seed Oil, metathesized Moringa Oil, metathesized Neem Oil, metathesized Olive Oil, metathesized Palm Oil, metathesized Palm Kernel Oil, metathesized Peach Kernel Oil, metathesized Peanut Oil, metathesized Pecan Oil, metathesized Pennycress oil, metathesized Perilla Seed Oil, metathesized Pistachio Oil, metathesized Pomegranate Seed Oil, metathesized Pongamia oil, metathesized Pumpkin Seed Oil, metathesized Raspberry Oil, metathesized Red Palm Olein, metathesized Rice Bran Oil, metathesized Rosehip Oil, metathesized Safflower Oil, metathesized Seabuckthorn Fruit Oil, metathesized Sesame Seed Oil, metathesized Shea Olein, metathesized Sunflower Oil, metathesized Soybean Oil, metathesized Tonka Bean Oil, metathesized Tung Oil, metathesized Walnut Oil, metathesized Wheat Germ Oil, metathesized High Oleoyl Soybean Oil, metathesized High Oleoyl Sunflower Oil, metathesized High Oleoyl Safflower Oil, metathesized High Erucic Acid Rapeseed Oil, and mixtures thereof.

L. A lubricating member according to Paragraph A or D, further comprising a water soluble polymer.

M. The lubricating member according to Paragraph L, wherein said water soluble polymer is selected from polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, guars, cellulose, modified cellulose and mixtures thereof.

N. The lubricating member according to Paragraph L, wherein said water soluble polymer is polyethylene oxide having an average molecular weight of at least 300000, preferably from 300,000 to 8 Million, more preferably from 1 million to 5 million, most preferably from 2 to 3 million.

O. The lubricating member according to Paragraph L, wherein said water soluble polymer further comprises from 0.01% to 50%, preferably from 2% to 40%, by weight of the lubricating material of a copolymer of polyethylene oxide and polypropylene oxide.

P. The lubricating member according to Paragraph L, wherein said polyethylene oxide polymer is present at a level of from 15% to 70%, preferably from 20% to 60%, more preferably from 25% to 50% by weight of the lubricating material.

Q. The lubricating member according to Paragraph A or D, wherein said lubricating member further comprises from 1% to 50% by weight of a water insoluble material, preferably selected from polyethylene, polypropylene, polystyrene, high impact polystyrene, butadiene styrene copolymer, polyacetal, acrylonitrile-butadiene styrene copolymer, ethylene vinyl acetate copolymer and mixtures thereof.

R. A hair removal cartridge having a front end and an opposing rear end, the hair removal cartridge comprising:
  a. at least one hair removal member positioned between said front end and said rear end; and
  b. at least one lubricating member according to any one of the preceding claims.

S. A hair removal device comprising:
  a. a hair removal cartridge according to Paragraph A, and
  b. a handle permanently or removably attached to said hair removal cartridge.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A lubricating member for use on a hair removal device, said lubricating member comprising a lubricating material comprising from 1% to 99% by weight of metathesized unsaturated polyol ester, said metathesized unsaturated polyol ester having a free hydrocarbon content, based on total weight of said metathesized unsaturated polyol ester, of from about 0.1% to about 3% and one or more of the following properties:
   (i) a weight average molecular weight of from about 5,000 Daltons to about 50,000 Daltons;
   (ii) an oligomer index from greater than 0 to 1; and
   (iii) an iodine value of from about 30 to about 200;
wherein said lubricating member is manufactured using one of an extrusion, injection molding, compression, or hot melt process, wherein:
   said extrusion process comprises heating to between 150° C. and 200° C.;
   said injection molding process comprises heating to between 165° C. and 250° C.;
   said compression process comprises applying a compression force of at least one kN; and
   said hot melt process comprises heating to between 55° C. and 85° C. and applying a pressure.

2. A lubricating member for use on a hair removal device, said lubricating member comprising a lubricating material comprising from 1% to 99% by weight of a composition comprising:
   a) a metathesized unsaturated polyol ester, said metathesized unsaturated polyol ester having a weight average molecular weight of from about 2,000 Daltons to about 50,000 Daltons and a free hydrocarbon content, based on total weight of said metathesized unsaturated polyol ester, of from about 0.1% to about 5% and one or more of the following properties:
      (i) an oligomer index from greater than 0 to 1; and
      (ii) an iodine value of from about 8 to about 200
   wherein said lubricating member is manufactured using one of an extrusion, injection molding, compression, or hot melt process, wherein:
      said extrusion process comprises heating said composition to between 150° C. and 200° C.;

said injection molding process comprises said composition heating to between 165° C. and 250° C.;

said compression process comprises applying a compression force of at least one kN to said composition; and said hot melt process comprises heating said composition to between 55° C. and 85° C. and applying a pressure.

3. The lubricating member according to claim 2, wherein said metathesized unsaturated polyol ester has an iodine value of from about 10 to about 200.

4. The lubricating member according to claim 2, wherein said metathesized unsaturated polyol ester has an oligomer index from about 0.001 to 1.

5. The lubricating member according to claim 1, wherein said lubricating material comprises from about 0.1% to about 50% by weight of said metathesized unsaturated polyol ester.

6. The lubricating member according to claim 1, wherein the metathesized unsaturated polyol ester is metathesized at least once.

7. The lubricating member according to claim 1, wherein said metathesized unsaturated polyol ester is derived from a natural polyol ester and/or a synthetic polyol ester.

8. The lubricating member according to claim 1, wherein said metathesized unsaturated polyol ester is selected from the group consisting of metathesized Abyssinian oil, metathesized Almond Oil, metathesized Apricot Oil, metathesized Apricot Kernel oil, metathesized Argan oil, metathesized Avocado Oil, metathesized Babassu Oil, metathesized Baobab Oil, metathesized Black Cumin Oil, metathesized Black Currant Oil, metathesized Borage Oil, metathesized Camelina oil, metathesized Carinata oil, metathesized Canola oil, metathesized Castor oil, metathesized Cherry Kernel Oil, metathesized Coconut oil, metathesized Corn oil, metathesized Cottonseed oil, metathesized Echium Oil, metathesized Evening Primrose Oil, metathesized Flax Seed Oil, metathesized Grape Seed Oil, metathesized Grapefruit Seed Oil, metathesized Hazelnut Oil, metathesized Hemp Seed Oil, metathesized Jatropha oil, metathesized Jojoba Oil, metathesized Kukui Nut Oil, metathesized Linseed Oil, metathesized Macadamia Nut Oil, metathesized Meadowfoam Seed Oil, metathesized Moringa Oil, metathesized Neem Oil, metathesized Olive Oil, metathesized Palm Oil, metathesized Palm Kernel Oil, metathesized Peach Kernel Oil, metathesized Peanut Oil, metathesized Pecan Oil, metathesized Pennycress oil, metathesized Perilla Seed Oil, metathesized Pistachio Oil, metathesized Pomegranate Seed Oil, metathesized Pongamia oil, metathesized Pumpkin Seed Oil, metathesized Raspberry Oil, metathesized Red Palm Olein, metathesized Rice Bran Oil, metathesized Rosehip Oil, metathesized Safflower Oil, metathesized Seabuckthorn Fruit Oil, metathesized Sesame Seed Oil, metathesized Shea Olein, metathesized Sunflower Oil, metathesized Soybean Oil, metathesized Tonka Bean Oil, metathesized Tung Oil, metathesized Walnut Oil, metathesized Wheat Germ Oil, metathesized High Oleoyl Soybean Oil, metathesized High Oleoyl Sunflower Oil, metathesized High Oleoyl Safflower Oil, metathesized High Erucic Acid Rapeseed Oil, and mixtures thereof.

9. The lubricating member according to claim 1, further comprising a water soluble polymer.

10. The lubricating member according to claim 9, wherein said water soluble polymer is selected from polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, guars, cellulose, modified cellulose, and mixtures thereof.

11. The lubricating member according to claim 9, wherein said water soluble polymer is polyethylene oxide having an average molecular weight of at least 300000.

12. The lubricating member according to claim 9, wherein said water soluble polymer further comprises from 0.01% to 50% by weight of the lubricating material of a copolymer of polyethylene oxide and polypropylene oxide.

13. The lubricating member according to claim 9, wherein said water soluble polymer comprises a polyethylene oxide polymer that is present at a level of from 15% to 70% by weight of the lubricating material.

14. The lubricating member according to claim 1, wherein said lubricating member further comprises from 1% to 50% by weight of a water insoluble material, selected from polyethylene, polypropylene, polystyrene, high impact polystyrene, butadiene styrene copolymer, polyacetal, acrylonitrile-butadiene styrene copolymer, ethylene vinyl acetate copolymer, and mixtures thereof.

15. The lubricating member according to claim 2, wherein said free hydrocarbon content is from about 0.1% to about 3%.

16. The lubricating member according to claim 1, wherein said metathesized unsaturated polyol ester has a weight average molecular weight of from about 5,000 Daltons to about 50,000 Daltons.

* * * * *